(12) United States Patent
Jiang et al.

(10) Patent No.: US 8,311,606 B2
(45) Date of Patent: Nov. 13, 2012

(54) CONDUCTIVE POLYMER PATTERNED ELECTRODE FOR PACING

(75) Inventors: Xiangchun Jiang, St. Paul, MN (US); Kevin J. Ely, Blaine, MN (US); Jeannette C. Polkinghorne, St. Anthony, MN (US)

(73) Assignee: Cardiac Pacemakers Inc., St. Paul, MN (US)

( * ) Notice: Subject to any disclaimer, the term of this patent is extended or adjusted under 35 U.S.C. 154(b) by 1128 days.

(21) Appl. No.: 11/533,644

(22) Filed: Sep. 20, 2006

(65) Prior Publication Data
US 2008/0071338 A1 Mar. 20, 2008

(51) Int. Cl.
*A61B 5/04* (2006.01)

(52) U.S. Cl. .................. 600/395; 600/372; 600/373

(58) Field of Classification Search .......... 600/372–373, 600/395
See application file for complete search history.

(56) References Cited

U.S. PATENT DOCUMENTS

| | | | |
|---|---|---|---|
| 4,226,247 A * | 10/1980 | Hauser et al. | 600/391 |
| 4,524,087 A * | 6/1985 | Engel | 427/2.12 |
| 4,542,752 A * | 9/1985 | DeHaan et al. | 607/119 |
| 4,844,099 A | 7/1989 | Skalsky et al. | |
| 4,968,390 A * | 11/1990 | Bard et al. | 205/115 |
| 5,078,138 A * | 1/1992 | Strand et al. | 600/372 |
| 5,345,934 A * | 9/1994 | Highe et al. | 600/372 |
| 5,370,115 A * | 12/1994 | Ogawa et al. | 600/372 |
| 5,524,338 A * | 6/1996 | Martyniuk et al. | 29/825 |
| 5,529,579 A | 6/1996 | Alt et al. | |
| 6,103,033 A * | 8/2000 | Say et al. | 156/73.1 |
| 6,444,400 B1 * | 9/2002 | Cloots et al. | 430/311 |
| 6,501,994 B1 | 12/2002 | Janke et al. | |
| 6,718,628 B2 * | 4/2004 | Munshi | 29/825 |
| 6,757,556 B2 * | 6/2004 | Gopinathan et al. | 600/372 |
| 6,799,076 B2 * | 9/2004 | Gelb et al. | 607/121 |
| 7,463,917 B2 * | 12/2008 | Martinez | 600/395 |
| 2002/0183817 A1 | 12/2002 | Van Venrooij et al. | |
| 2006/0003090 A1 | 1/2006 | Rodger et al. | |
| 2006/0111626 A1 | 5/2006 | Rossing et al. | |

FOREIGN PATENT DOCUMENTS

| | | |
|---|---|---|
| JP | 2001101937 A | 4/2001 |
| JP | 2002516731 A | 6/2002 |
| JP | 2002528235 A | 9/2002 |
| JP | 2005007175 A | 1/2005 |
| WO | WO2006060705 A1 | 6/2006 |
| WO | 2006078700 | 7/2006 |

OTHER PUBLICATIONS

E. De Giglio et al., "Electropolymerization of pyrrole on titanium substrates for the future development of new biocompatible surfaces," Biomaterials, vol. 22 (2001) pp. 2609-2616.

(Continued)

*Primary Examiner* — Nicole F Lavert
(74) *Attorney, Agent, or Firm* — Faegre Baker Daniels LLP

(57) ABSTRACT

The present invention is an apparatus and method for making a polymer patterned electrode for cardiac pacing and sensing. The electrode surface includes a polymer overlayed on an electrode. The polymer layer is patterned to form an electrode surface consisting of a polymer and a conductive metal surface. The electrode can be made of a high or low impedance electrode by changing the conductivity of the polymer. Furthermore, the electrode surface texture can be optimized with a micro pattern that may enhance the biocompatibility. The polymer may be conductive or insulative.

14 Claims, 8 Drawing Sheets

OTHER PUBLICATIONS

Guixin Shi, et al., "A novel electrically conductive and biodegradable composite made of polypyrrole nanoparticles and polylactide," Biomaterials, vol. 25 (2004) pp. 2477-2488.

T. V. Vernitskaya et al., "Polypyrrole: a conducting polymer; its synthesis, properties and applications," Russian Chemical Reviews, vol. 66 (1997) pp. 443-457.

Harshad Borgaonkar, "Conductive Polymeric Coating with Optional Biobeneficial Topcoat for a Medical Lead", U.S. Appl. No. 11/277,858, filed Mar. 29, 2006.

International Search Report and Written Opinion of international application No. PCT/US20071073997, filed Jul. 20, 2007, mailed Jan. 25, 2008, 14 pp.

* cited by examiner

Polypyrole coating w/o Patterning

Polypyrole coating w & w/o Patterning

CONDUCTIVE POLYMER PATTERNED ELECTRODE FOR PACING

FIELD OF THE INVENTION

The present invention relates to pacing electrodes. More specifically, the present invention is an apparatus and method for making a conductive polymer patterned electrode for cardiac pacing and sensing.

BACKGROUND OF THE INVENTION

When functioning properly, the human heart maintains its own intrinsic rhythm and is capable of pumping adequate blood throughout the body's circulatory system. However, some people have irregular cardiac rhythms, referred to as cardiac arrhythmias. Such arrhythmias result in diminished blood circulation. One manner of treating cardiac arrhythmias includes the use of a cardiac rhythm management system. Such systems may be implanted in a patient to deliver electrical pulses to the heart.

Cardiac rhythm management systems include, for example, pacemakers (also referred to as "pacers"), defibrillators (also referred to as "cardioverters") and cardiac resynchronization therapy ("CRT") devices. These systems use conductive leads having one or more electrodes to deliver pulsing energy to the heart. Leads are usually positioned on or in the ventricle or the atrium and the lead terminal pins are attached to a pacemaker or defibrillator which is implanted subcutaneously or in the abdomen.

Cardiac pacing leads are well known and widely employed for carrying pulse stimulation signals to the heart from a battery operated pacemaker, or other pulse generating means, as well as for monitoring, or sensing, electrical activity of the heart from a location outside of the body. Electrodes are also used to stimulate the heart in an effort to mitigate bradycardia or terminate tachycardia or other arrhythmias. In all of these applications, it is highly desirable to optimize electrical performance characteristics of the electrode/tissue interface. Such characteristics include minimizing the threshold voltage necessary to depolarize adjacent cells, maximizing the electrical pacing impedance to prolong battery life, and minimizing sensing impedance to detect intrinsic signals.

For cardiac pacemaker leads and electrodes, pacemaker implant lifetime may be partially determined by the energy delivered per pulse. Other factors that determine the energy used by the pacemaker include the electrode size, material, surface nature, and shape, the body tissue or electrolyte conductivity, and the distance separating the electrode and the excitable tissue. The pacemaker will have a longer life if the energy delivered per pulse is maintained at a minimum. The energy delivered cannot be reduced too far, however, as a critical amount of current is required for pacing. The pacing (or stimulation) threshold is a reflection of the electrical energy required for a pulse to initiate a cardiac depolarization. The saved energy can be used to provide for more features in the pacemaker. Furthermore, reducing the size of the electrode is not necessarily an optimal solution as then the electrode may be too small to properly and securely fix to the heart. Moreover, smaller electrodes may have reduced sensing capacity.

Leads are often made of some conductive metal or include a conductive metal surface coating like titanium, platinum, platinum iridium or iridium oxide. Electrical current passed through these leads, however, may cause undesired chemical reactions such as water electrolysis, oxidation of soluble species, reactions that result in the formation of gases, and metal dissolution from the electrode. The non-ideal biocompatibility of the metals used to make electrodes may therefore waste the energy provided to the electrode and result in decreased efficiency. In addition, the electric performance may be affected by the geometry of the electrode itself.

A continued need therefore exists for improved electrodes for pacing and sensing.

BRIEF SUMMARY OF THE INVENTION

In one aspect the present invention includes a method of making an implantable electrode by forming a polymer layer on a conductive metal substrate and patterning the polymer layer to form an electrode surface that includes a polymer with exposed conductive metal substrate.

Another aspect of the present invention includes an implantable electrode with a conductive electrode substrate and a patterned conductive or insulative coating placed on the electrode substrate.

Yet another aspect of the present invention includes an implantable lead for use with a cardiac pacemaker that includes an electrical conductor having a proximal end and a distal end, an insulative sheath covering said conductor, an electrical connector coupled to said proximal end of said conductor and an electrode coupled to said distal end of said conductor, said electrode including a polymer placed on the surface of the electrode, the polymer being patterned in a desired pattern.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION OF THE INVENTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

The present invention is an electrode with a patterned polymer coating for high impedance pacing and a relates to method of making the same. The method may include placing a polymer coating on a metallic surface and then patterning the coating such that both the metal and polymer are exposed on the surface of the electrode. The electrode may be used for high impedance pacing and sensing. In further embodiments the electrode may also be used for non-high impedance pacing.

The patterned surface electrode may achieve a high pacing impedance with no constraint of physical geometry in the electrode design. The patterned surface electrode may also achieve high efficiency pacing with an improved biocompatibility. The high impedance achieved using the present invention may allow for prolonged battery life, improved electrode fixation, and reduced perforation. The electrode may also serve as vehicle for drug coating and controlled drug delivery and may promote tissue in-growth. The tissue in-growth may be enhanced by the selected pattern such that the formation of a fibrotic capsule is reduced.

In one embodiment of the present invention the size and shape of the polymer pattern may be optimized for efficient pacing and sensing. Such optimization may result in exposing an optimized amount of polymer surface area and conductive metal surface area. The thickness of the polymer may be further optimized in terms of sensing and energy consumption. Such optimization may result in a smaller amount of the conductive metal of the electrode being in contact with the heart but still a high current density.

The term "lead" is used herein in its broadest sense and includes any lead configuration available in the art, including, but not limited to, a stimulation lead, a sensing lead or a combination thereof. In one embodiment the lead may be adapted for active fixation. In another embodiment the lead may be adapted for passive fixation. In yet another embodiment the lead may be adapted for bipolar stimulation. In another embodiment the lead may be tripolar or quadrupolar. In another embodiment the lead may include multiple electrodes.

Figure 1:
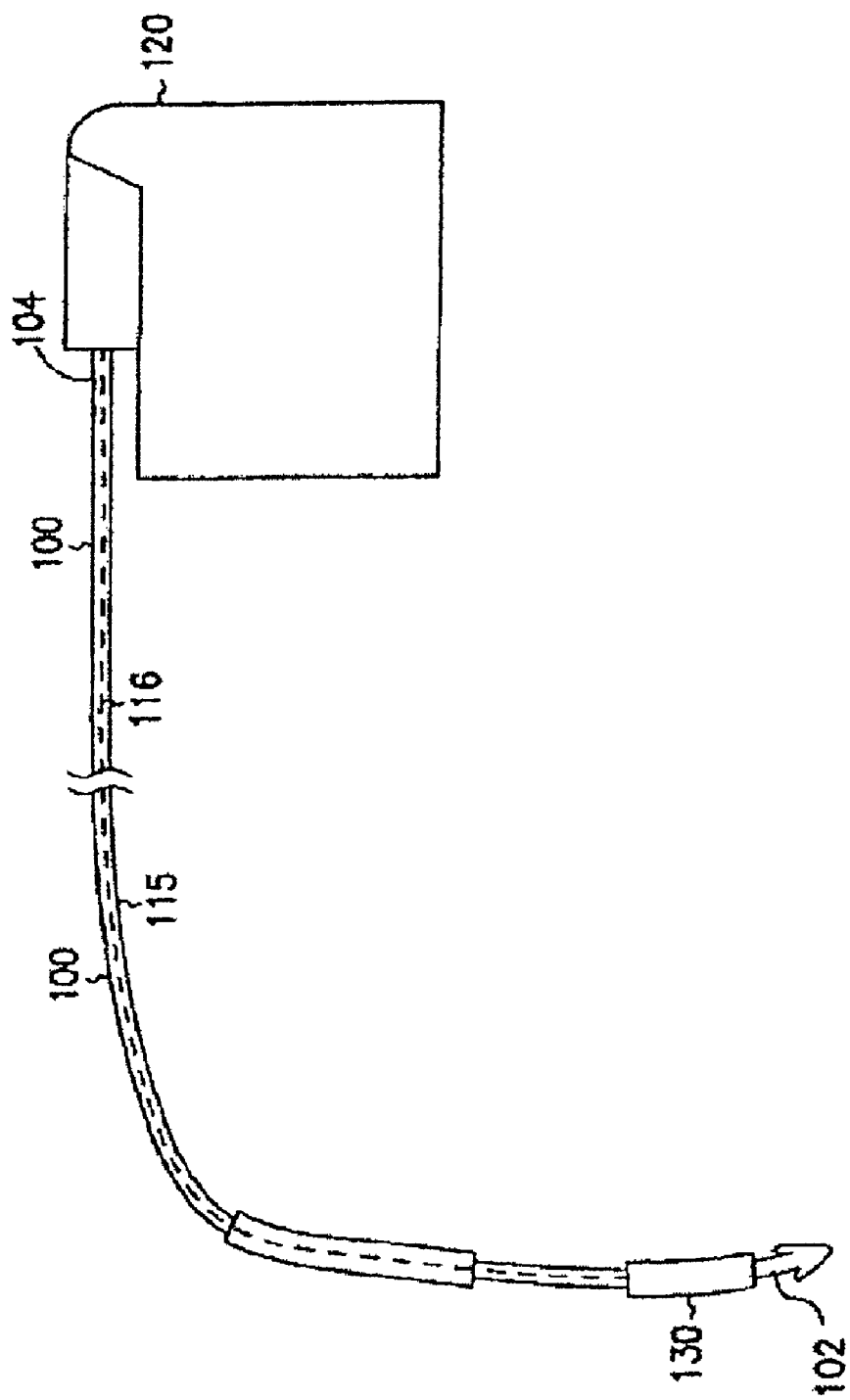
FIG. 1 illustrates a side plan view of an electrode attached to a pulse generator via a lead.

FIG. 1 illustrates a lead 100 for delivering electrical pulses to stimulate a heart and/or for receiving electrical pulses to monitor the heart. The lead 100 has a distal end 102 adapted for implant within a body and a proximal end 104. The proximal end 104 has a connector terminal (not shown) which electrically connects the various electrodes and conductors within the lead 100 to a unit 120. The unit 120 may contain electronics to sense various electrical signals of the heart and also to produce current pulses for delivery to the heart. The terminal connector provides for the electrical connection between the lead 100 and the unit 120.

The lead 100 may include a lead body 115, an elongated conductor 116 contained within the lead body 115, and at least one electrode 130. The lead body 115 may be covered by a biocompatible insulating material such as silicone rubber or another insulating material. In one embodiment, the electrode 130 is disposed proximate to the distal end 102 of the lead 100. In another embodiment, the electrode 130 is disposed between the distal end 102 and the proximal end 104 of the lead 100. The electrode 130 may be made of a metallic compound that operatively contains the elongated conductor 116.

The electrode may be made from a biocompatible metal or metallic compound such as from one or more of the group consisting of platinum, platinum iridium, iridium oxide, titanium, titanium nitride, titanium oxide, titanium oxynitride, titanium carbide, tantalum, tantalum oxide, tantalum nitride, tantalum oxynitride, and combinations thereof Further electrodes may be formed of one base material and then include a capacitive coating made out of any of the above conductive materials, in addition to other materials, such as, for example, NASICON. The capacitive coating may be deposited by a physical vapor deposition (PVD) process, such as sputtering, evaporation, ion implantation, or ion beam assisted deposition (IBAD). In further embodiments the capacitive coating may be a conductive polymer.

In one embodiment, lead 100 is adapted to deliver pacing energy to a heart. Some embodiments deliver defibrillation shocks to a heart. Unit 120 can be implanted in a surgically-formed pocket in a patient's chest or other desired location. The unit 120 generally includes electronic components to perform signal analysis, processing and control. The unit 120 can include a power supply such as a battery, a capacitor and other components housed in a case. The device can include microprocessors to provide processing and evaluation to determine ventricular defibrillation, cardioversion and pacing to a heart in response to cardiac arrhythmia including fibrillation, tachycardia and bradycardia.

In the present invention, the conductive metal of the electrode (or of the capacitive coating covering the conductive metal is coated with a polymer coating that is then patterned so as to expose both the metal electrode (or the coating thereon) and the polymer coating. The polymer may be more biocompatible than the metallic electrode surface. In one embodiment the polymer coating may be conductive. In other embodiments the polymer may be non-conductive (an insulator, or insulative).

Conductive polymers, also described as electroactive polymers, mainly comprise inherently conductive polymers (ICP) and conductive plastics. The latter are traditional plastics, such as thermoplastics, that may include conductive fillers, such as powdered metals or carbon (e.g., carbon black or fiber). The conductive polymer may be biocompatible conductive polymers that are made ionically conductive and that are mechanically stable over a desired period of time, such as, for example, polypyrrole. In further embodiments the conductive polymer may include, for example, polynaphthalene, polythiophene, Nafion, polyethylene oxide, and polyethyldioxythiophene (PEDOT). Other classes of conductive polymers include polyacetylenes, conductive polypyrrole polystyrene sulfonate, polythiophenes (PT), and polyanilines. Conductive polymers may also include EHPT (poly(3-(2-ethylhexyl)thiophene), ionomers (e.g., Nafion®), poly(3,4 ethylene dioxythiophene) (PEDOT) and PEDOT polystyrene sulfonate (PSS/PEDOT).

In one embodiment, the conductive polymers are biocompatible (e.g., the polymers are not toxic or injurious to living tissue). Use of conductive polymers can reduce pacing threshold and improve the sensing performance. Furthermore, inclusion of the polymer may improve upon the biocompatibility of the electrode. For example, the use of conductive polymers on an electrode allows for the presentation of an organic interface to biological tissue instead of a metallic interface (e.g., a metallic electrode) for a favorable biological response to the implant. Inflammatory and healing response of tissue can be controlled and altered to reduce necrosis in the area next to the lead and reduce the thickness of any resultant fibrotic capsule. An optional topcoat layer may also be present.

Dopants may also be used with the inherently conductive polymers or with polymers that are not conductive (as discussed further below). Doping may enhance the conductivity of a polymer and provide a lower energy threshold for conductivity. Dopants may also help to specifically control the conductivity characteristics. There are many methods and materials useful in doping that may be known to those skilled in the art. Doping materials can include, but are not limited to chloride, polystyrene sulfonate (PSS), dodecylbenzenesulfonate, polystyrenesulfonate, naphthalene sulfonate, and lithium perchlorate. In one embodiment, electrically conductive coatings are deposited on the polymer surface or electrically conductive particles are blended with polymer.

Insulative polymers may also be used to reduce the exposed surface area and to increase the pacing impedance. One non-conductive polymer may include Parylene. Parylene may come in a variety of forms, including N, C and D. Parylene N is a poly-para-xylylene. Parylene C is the same as Parylene N except for the substitution of a chlorine atom for one of the aromatic hydrogens. Parylene D includes two chorine atoms substituted for aromatic hydrogens. In further examples a borosilicate glass coating may be applied to the electrode surface as an insulative layer. Polymers may also include silicone rubbers, polyurethane, and homopolymers or copolymers of polyolefin, fluoropolymer, polyamide and polyester. The coating may be applied in a pattern using a mask or may further be coated and then patterned with a laser.

In one embodiment for applying the polymer, at least one polymer to be coated on the electrode 130 may be mixed with a solvent to provide a solution or mixture. Examples of such solvents include water, alcohol, cyclohexanone, acetone, acetonitrile, and combinations thereof. The solution can be applied to at least a portion or all of a lead 100 and/or electrode 130 by, for example, spray coating. After the solvent in the solution is evaporated, a layer containing the polymer remains on the surface of the lead 100 and/or electrode 130. The process can be repeated as many times as desired to create layers of a desired thickness. Alternatively, the polymer can be applied to the lead 100 and/or electrode 130 by dip-coating, brush-coating, drop coating, electrospray coating, electrochemical deposition, electrospinning, sputtering or by electrodeposition. In further embodiments the polymer may be coated on the surface of the electrode by chemical deposition, plasma coating, or bipolar electrodeposition. In addition, the polymer can be patterned by laser etching, masking, or photoetching. These and other methods are well known to those of skill in the art.

In one embodiment, conductive polymers such as polypyrrole or PEDOT can be formed by passing a current through an electrode while the electrode is immersed in an aqueous solution of the monomer. This leads to the formation of a coating that is formed on the electrode. The coating may incorporate other molecules or dopants that are present in the solution while it is forming (e.g., therapeutic agents or biomolecules promoting attachment to tissue).

Spray coating may allow for greater control of coating placement which may allow for selectively coating one area of the lead and/or electrode without contaminating other areas of the lead and/or electrode with the spray solution/mixture. Other benefits of spray coating may include decreased waste of coating solution/mixture and uniform coating on the device (e.g., along a lead body or on an electrode).

In further embodiments a protein may be incorporated into the polymer placed on the surface of the electrode or another polymer applied to the electrode specifically for this purpose. One protein may include, for example, collagen. Further biobeneficial agents may also be utilized such as, for example, heparin. In still further embodiments, certain types of drugs or other biological agents can be incorporated into the polymer such that it undergoes controlled release during pacing. In such embodiments the drug or biological agent may be released due in part to the applied electrical flow.

In still further embodiments the electrode 130 may include a degradable protective coating 150 in addition to the capacitive coating 140. The degradable protective coating 150 may be a sacrificial coating that degrades over a pre-determined period of time so as to protect the electrode 130 from the formation of thrombi or other biological responses during the implantation procedure. In various embodiments the degradable protective coating 150 may be completely removed before or after the electrode 130 is in the final desired position.

In one embodiment the degradable protective coating 150 may include a hydrogel coating. The hydrogel coating may be constructed of a biocompatible coating 150 such as polyethylene glycol (PEG). The PEG may be in a variety of forms such as a copolymer, a cross-linked network, or a polymer blend. Such a hydrogel degradable protective coating 150 may aid or mediate tissue in-growth before it is degraded. In addition, the hydrogel degradable protective coating may serve to protect the electrode from blood coagulation during placement of the lead such that a preliminary thrombus does not form until after the electrode is in the desired position. Many hydrogels, such as those formed from PEG, may also display lubricious characteristics and may therefore further aid in the insertion of the electrode into the coronary vein. In further embodiments the polymer may be doped with biocompatible chemicals and/or drugs for better biocompatibility, improved pacing and sensing, improved retention on the surface of the electrode, and time release of a desired agent.

PEG comes in a variety of high or low molecular weights which can be selected depending on the desired degradation properties. The PEG can be deposited on the electrode by dip coating the electrode. In further embodiments a solution containing the polyethylene glycol may be syringe coated on the electrode.

In further embodiments, the surface of the electrode may be protected via other degradable materials such as mannitol, or other degradable polymers, such as polylactic-co-glycolic acid (PLGA) or any polymer. The selected polymer may have surface or bulk degradation properties that can be adjusted so as to dissolve over time to protect the electrode 130 from thrombus formation or other undesirable biological processes until the electrode 130 is in its final implant position.

Figure 9:
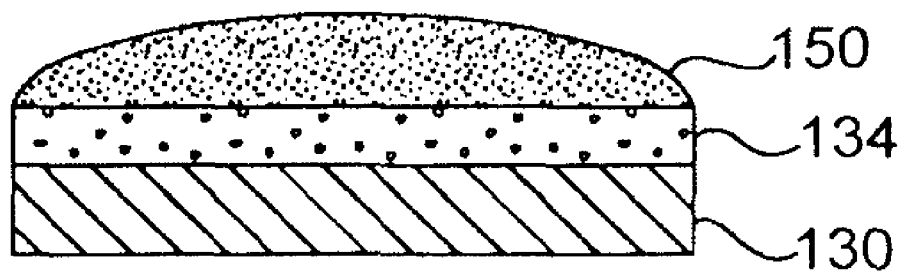
FIG. 9 is a schematic view on an electrode provided in accordance with another embodiment of the present invention.

The drug eluting properties of certain materials that can be used as the degradable protective coating 150, such as PEG, may also provide a site specific vehicle for delivery of drugs, therapeutic agents and other biologically active agents. Such agents may help to further reduce blood clotting and thrombi formation. One drug loaded directly into or on the degradable protective coating 150, or the porous surface 134 (FIG. 9), may include dexamethasone acetate. Dexamethasone acetate may contribute to the reduction of fibrous capsule growth and decrease the pacing threshold. In still further embodiments degradable protective coating materials 150 may be formed as a copolymer or a blend with other polymers to achieve desired degradation or drug eluting characteristics. Other drugs may be loaded into the pores, doped in to or on to the degradable polymer, or applied to the polymer coating. Further drugs may include, for example, clobetesol, everoliums, sirolimus, or dexamethasone phosphate.

The therapeutic agent may include, but is not limited to an anti-inflammatory, anti-proliferative, anti-arrhythmic, anti-migratory, anti-neoplastic, antibiotic, anti-restenotic, anti-coagulation, anti-clotting (e.g., heparin, coumadin, aspirin), anti-thrombogenic or immunosuppressive agent, or an agent that promotes healing, such as a steroid (e.g., a glucocorticosteriod), and/or re-endothelialization or combinations thereof. In essence, any drug or biologically active agent which can serve a useful therapeutic, prophylactic or even diagnostic function when released into a patient can be used.

EXAMPLE 1

Figure 2:
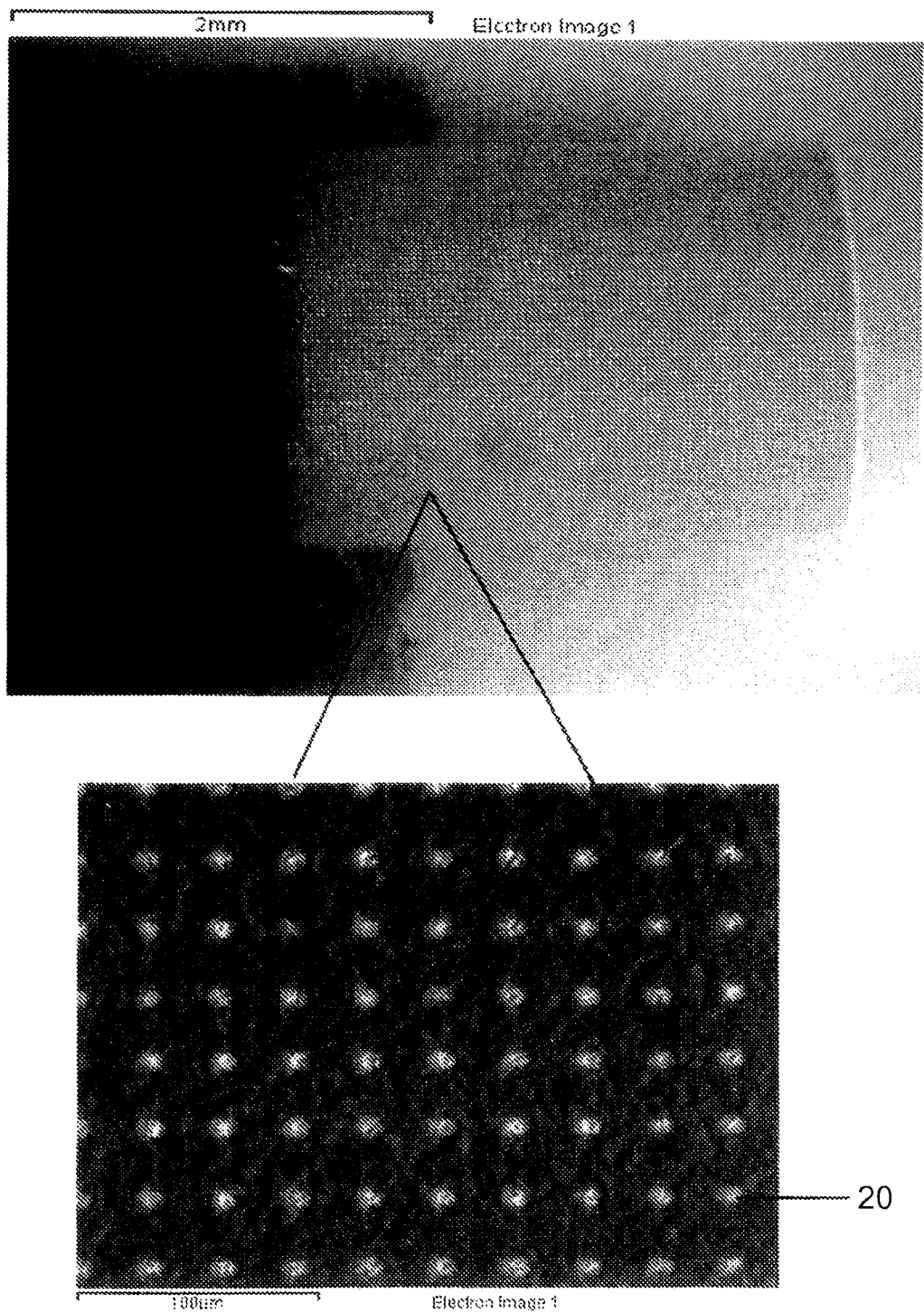
FIG. 2 illustrates a Parylene insulative layer on an electrode after being patterned in a first pattern.
Figure 3:
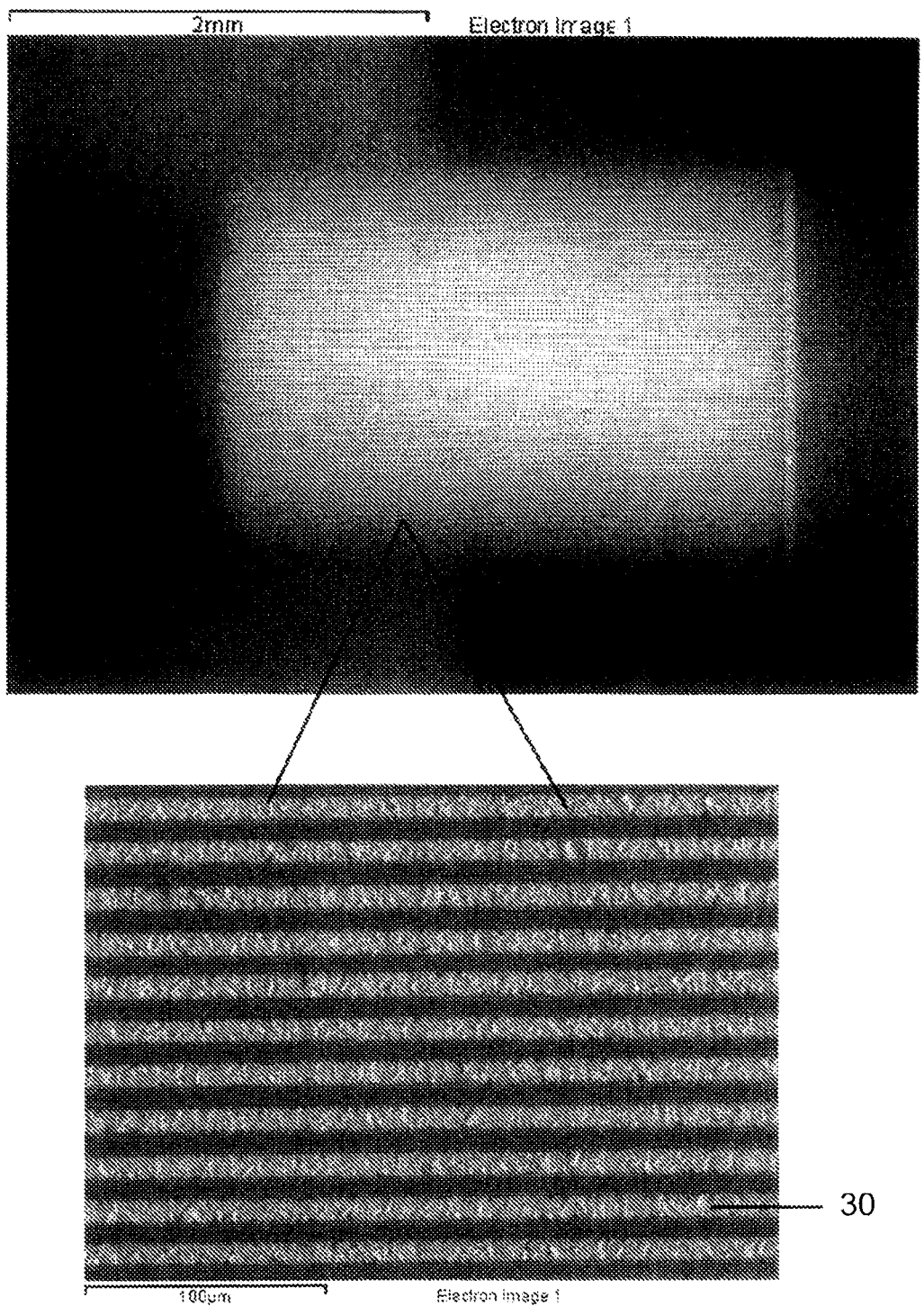
FIG. 3 illustrates a Parylene insulative layer on an electrode after being patterned in a second pattern.

In a first example Parylene may be pattern coated on the surface of the electrode. As previously discussed, Parylene is an insulative polymer. In the present example the Parylene was coated on a platinum iridium ring by vapor deposition using methods known to those in the art. The resultant Parylene coating was about 5 μm thick. In alternative embodiments the coating may be from less than 1 μm to as much or more than 25 μm thick. The Parylene formed a complete coating over the ring and was then patterned by laser etching to form surfaces as shown in FIGS. 2 and 3. In FIG. 2, the patterning was done by creating specific holes 20 in the Parylene coating to expose the platinum iridium ring. FIG. 3 illustrates patterned trenches 30 in the Parylene coating parallel to the long axis of the ring. In further embodiments, patterned trenches may go circumferentially around the ring. In still further embodiments, any pattern may be made in the Parylene layer by the laser. The laser etching of the present example was performed using an excimer laser with a wavelength of 264 nm.

In further embodiments the wavelength may be optimized depending on the desired patterning characteristics. Wavelengths may vary from about 185 nm up to about 1064 nm. In further embodiments other types of lasers may also be utilized. Utilization of laser etching allows for very fine control of the pattern formed. Optimization of the pattern may encourage or accelerate the growth of epithelial cells and therefore further reduce the pacing threshold required. In further embodiments the electrode material, in addition to the polymer pattern, may be etched as well.

The pacing impedance of a number of Parylene patterned electrodes of different thickness and different patterns was tested. Twelve rings were coated with Parylene at 2 μm thickness and 12 rings were coated with Parylene at 5 μm thickness. Each of four selected test patterns were then created on three rings of each coating thickness using the excimer laser. In a first pattern 5 μm holes in the Parylene were spaced at 25 μm (FIG. 2). In a second pattern 25 μm holes in the Parylene were spaced at 5 μm (not shown). A third pattern included alternating 10 μm Parylene and 10 μm metal substrate strips in a parallel orientation to the long axis of the ring (FIG. 3). A fourth pattern included alternating 10 μm Parylene and 10 μm metal substrate strips in a circumferential orientation to the ring (not shown).

Figure 5:
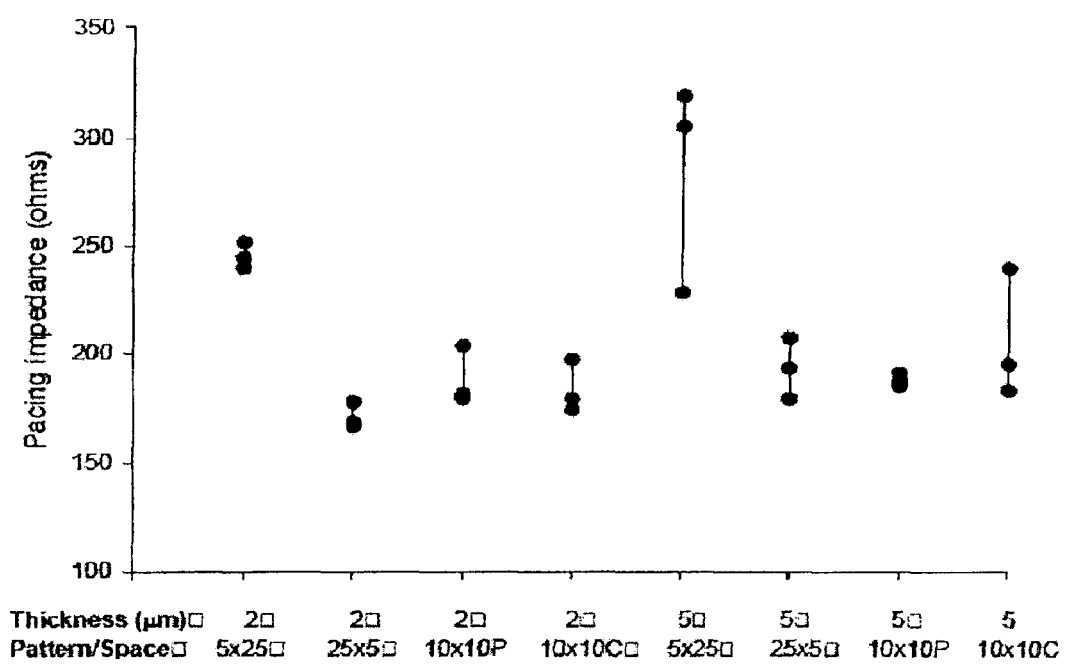
FIG. 5 is a chart showing the pacing impedance of the patterned electrodes of FIGS. 2 and 3.

The pacing impedance of a standard electrode without a coating is about 125 ohms. As illustrated in FIG. 5, the pacing impedance of the patterned Parylene coated electrode varied depending on the thickness of the coating and the pattern utilized, but was significantly improved in all cases, increasing the electrode pacing impedance approximately 30-250% compared to the standard electrode.

EXAMPLE 2

Figure 4:
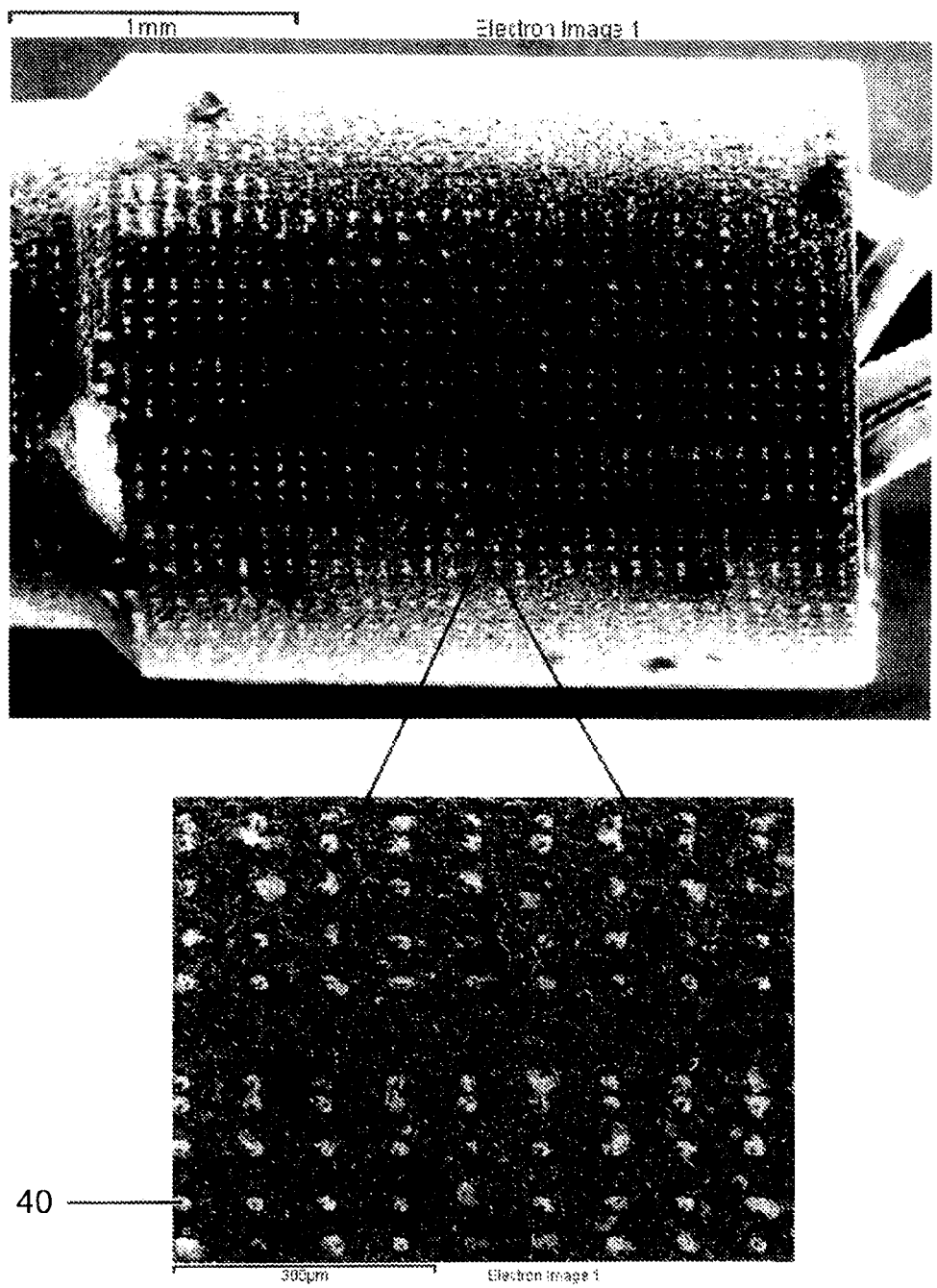
FIG. 4 illustrates a conductive polypyrrole layer after being patterned.

In a second embodiment the electrode was pattern coated with polypyrrole. Polypyrrole is a conductive polymer. The application of the polypyrrole was accomplished by dissolving pyrrole in a solution at 0.1 M with a KCl dopant at 0.1 M and electrochemically depositing the pyrrole on a platinum iridium ring electrode dipped in the solution. The coating was applied to a thickness of about 5 μm but in further embodiments may be up to or more than about 25 μm. The coating was then laser etched to expose the platinum iridium ring to form holes 40 in the pattern illustrated in FIG. 4. In further embodiments the concentration of the pyrrole in the solution may be varied as desired, for example, utilizing concentrations up to or more than 0.5 M.

Figure 6:
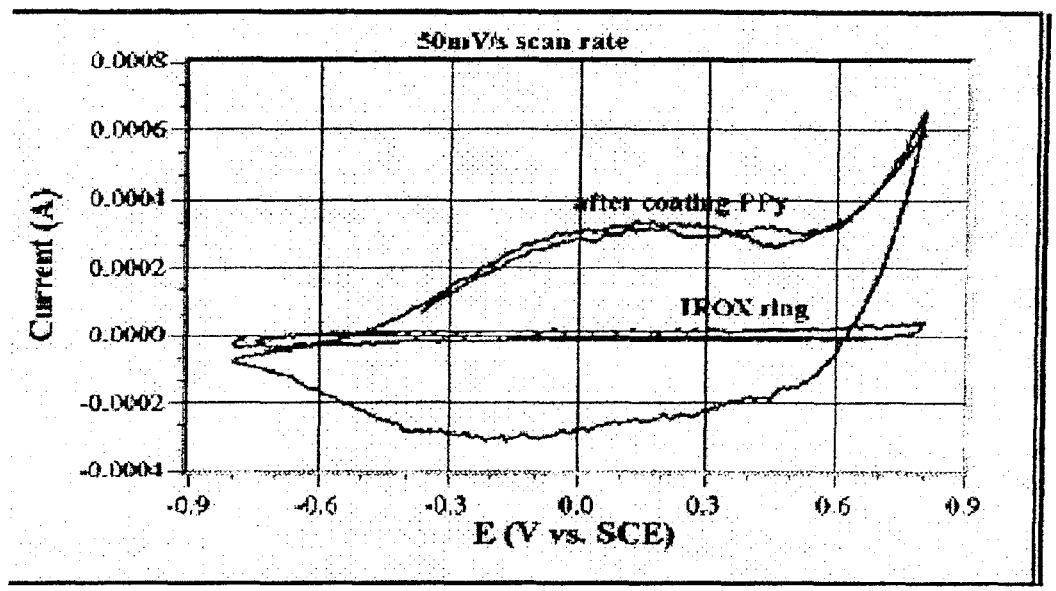
FIG. 6 illustrates a graph of a cyclic voltammetry scan of the conductivity of a ring electrode with a non-patterned polypyrrole conductive compared to a ring coated with an iridium oxide
Figure 7:
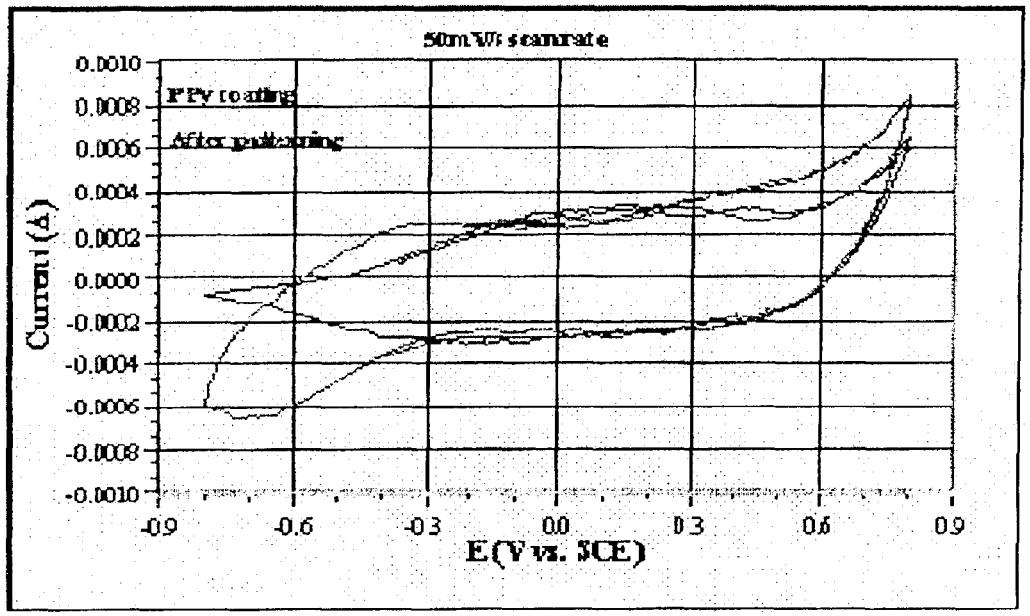
FIG. 7 illustrates a graph of a cyclic voltammetry scan of a ring electrode with the patterning of FIG. 5 compared to the conductive polymer without patterning.
Figure 8:
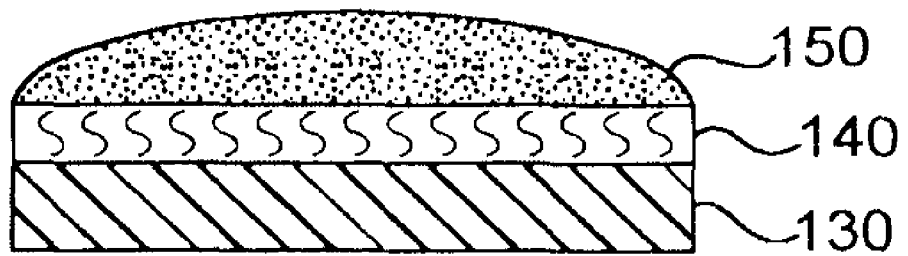
FIG. 8 is a schematic view on an electrode provided in accordance with an embodiment of the present invention.

The pattern coated ring was then tested by cyclic voltammetry versus a platinum ring coated with iridium oxide. As illustrated in FIG. 6, the platinum ring with the iridium oxide coating had a relatively small trace. The trace was significantly improved when a polypyrrole coating was applied, even without patterning, reflecting a significantly improved sensing ability. As illustrated in FIG. 7, however, the polypyrrole coating after patterning illustrated even further improvements. An optimized conductive coating that is patterned therefore improves the ability of the electrode to sense.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. A method of making an implantable electrode comprising:
   forming a polymer layer on a conductive electrode surface; and
   etching the conductive polymer layer to remove a portion of the conductive polymer layer in the form of a micropattern in the conductive polymer layer that exposes a portion of the conductive electrode surface.

2. The method of claim 1 wherein forming the conductive polymer layer further comprises depositing one or more of the group consisting of polypyrrole, polyethylene glycol, poly(naphthalene), poly(thiophene), PEDOT, Nafion, poly(ethylene) oxide or a combination thereof.

3. The method of claim 1 wherein forming the conductive polymer layer includes depositing the conductive polymer layer on the conductive electrode substrate, the conductive electrode substrate comprising any one of platinum, titanium, platinum iridium, iridium oxide, titanium nitride, titanium oxide, titanium oxynitride, titanium carbide, tantalum oxide, tantalum nitride, tantalum oxynitride, platinum, titanium, tantalum, or combinations thereof.

4. The method of claim 1 wherein the step of etching the conductive polymer layer comprises etching the conductive polymer layer with a laser.

5. The method of claim 1 wherein forming the polymer layer further comprises depositing the conducting polymer using one or more of dip-coating, brush-coating, drop coating, electrochemical deposition, electrospinning, sputtering or bipolar electrodeposited.

6. The method of claims 1 wherein forming the conducting polymer layer further includes forming a layer by physical vapor deposition.

7. The method of claim 1 further comprising loading a drug into or onto the polymer coating.

8. The method of claim 1 further comprising applying a degradable coating over the conductive polymer coating.

9. The method of claim 1 wherein etching the conductive polymer layer further comprises removing a portion of the conductive polymer layer to form a plurality of discrete holes in the conductive polymer to form the micro-pattern that exposes a portion of the conductive electrode surface.

10. The method of claim 1 wherein etching the conductive polymer layer further comprises removing strips of the conductive polymer layer to form the micro-pattern that exposes a portion of the conductive electrode surface.

11. The method according to claim 1, wherein the conductive polymer comprises polypyrrole.

12. The method according to claim 1, further comprising the step of depositing a capacitive coating onto the conductive electrode surface prior to forming the conductive polymer layer.

13. A method of making an implantable electrode comprising:
   coating a conductive electrode surface with a conductive polymer layer; and
   applying laser energy to the conductive polymer layer to remove a portion of the conductive polymer layer to form a plurality of micro-sized holes in the conductive polymer layer that expose the conductive electrode surface.

14. The method of claim 13 wherein the micro-sized holes have a diameter of no more than 25 microns.

* * * * *